United States Patent
Kim et al.

(10) Patent No.: US 11,072,621 B2
(45) Date of Patent: Jul. 27, 2021

(54) METHIONINE-METAL CHELATE AND MANUFACTURING METHOD THEREOF

(71) Applicant: CJ CHEILJEDANG CORPORATION, Seoul (KR)

(72) Inventors: Jun-Woo Kim, Seoul (KR); Min Kyu Kang, Seoul (KR); Gyeonghwan Kim, Seoul (KR); Il Chul Kim, Seoul (KR); Juun Park, Seoul (KR); Yong Bum Seo, Seoul (KR); In Sung Lee, Seoul (KR); Jun Young Jung, Seoul (KR); Je-won Hong, Seoul (KR)

(73) Assignee: GJ CHEILJEDANG CORPORATION, Seoul (KR)

(*) Notice: Subject to any disclaimer, the term of this patent is extended or adjusted under 35 U.S.C. 154(b) by 0 days.

(21) Appl. No.: 16/630,902

(22) PCT Filed: Jul. 6, 2018

(86) PCT No.: PCT/KR2018/007691
§ 371 (c)(1),
(2) Date: Jan. 14, 2020

(87) PCT Pub. No.: WO2019/013498
PCT Pub. Date: Jan. 17, 2019

(65) Prior Publication Data
US 2020/0157121 A1    May 21, 2020

(30) Foreign Application Priority Data
Jul. 14, 2017   (KR) .......... 10-2017-0089641

(51) Int. Cl.
*C07F 3/06*   (2006.01)
*A23K 20/142*   (2016.01)
(Continued)

(52) U.S. Cl.
CPC .............. *C07F 3/06* (2013.01); *A23K 20/142* (2016.05); *C01F 11/24* (2013.01); *C07C 319/20* (2013.01);
(Continued)

(58) Field of Classification Search
None
See application file for complete search history.

(56) References Cited

U.S. PATENT DOCUMENTS 6,407,138 B1   6/2002   Ashmead et al.
6,710,079 B1   3/2004   Ashmead et al.
(Continued)

FOREIGN PATENT DOCUMENTS

CN   102491927 A       6/2012
IN       197924   *   2/2007
(Continued)

OTHER PUBLICATIONS

International Search Report dated Nov. 8, 2018 from International Application No. PCT/KR2018/007691, 4 pages with English translation.
(Continued)

*Primary Examiner* — Amy C Bonaparte
(74) *Attorney, Agent, or Firm* — MH2 Technology Law Group, LLP

(57) ABSTRACT

The present disclosure relates to a preparation method of a methionine-metal chelate, and the methionine-metal chelate, which is prepared by first reacting $Ca(OH)_2$ and methionine and adding metal chloride salts, can be used as feeds and feed additives.

9 Claims, 1 Drawing Sheet

(51) Int. Cl.
*C01F 11/24* (2006.01)
*C07C 319/20* (2006.01)
*C07C 323/58* (2006.01)
*C07F 13/00* (2006.01)
*C07F 15/02* (2006.01)
*C07F 1/08* (2006.01)

(52) U.S. Cl.
CPC .............. *C07C 323/58* (2013.01); *C07F 1/08* (2013.01); *C07F 13/005* (2013.01); *C07F 15/025* (2013.01)

(56) References Cited

U.S. PATENT DOCUMENTS

| | | | |
|---|---|---|---|
| 7,087,775 B2 | 8/2006 | Lee et al. | |
| 2005/0283013 A1* | 12/2005 | Lee | C07C 319/20 556/116 |

FOREIGN PATENT DOCUMENTS

| | | | |
|---|---|---|---|
| JP | 2002-069051 A | 3/2002 | |
| JP | 2010-090064 A | 4/2010 | |
| KR | 10-0509141 | 8/2005 | |
| KR | 10-0583274 | 5/2006 | |
| KR | 10-0860778 | 9/2008 | |
| WO | 95/13700 A2 | 5/1995 | |
| WO | WO-0204351 A1 * | 1/2002 | .............. C01F 11/24 |
| WO | 2013/136030 A2 | 9/2013 | |

OTHER PUBLICATIONS

Extended European Search Report dated Dec. 23, 2020 for corresponding European Patent Application No. 18832072.5, 10 pages.

* cited by examiner

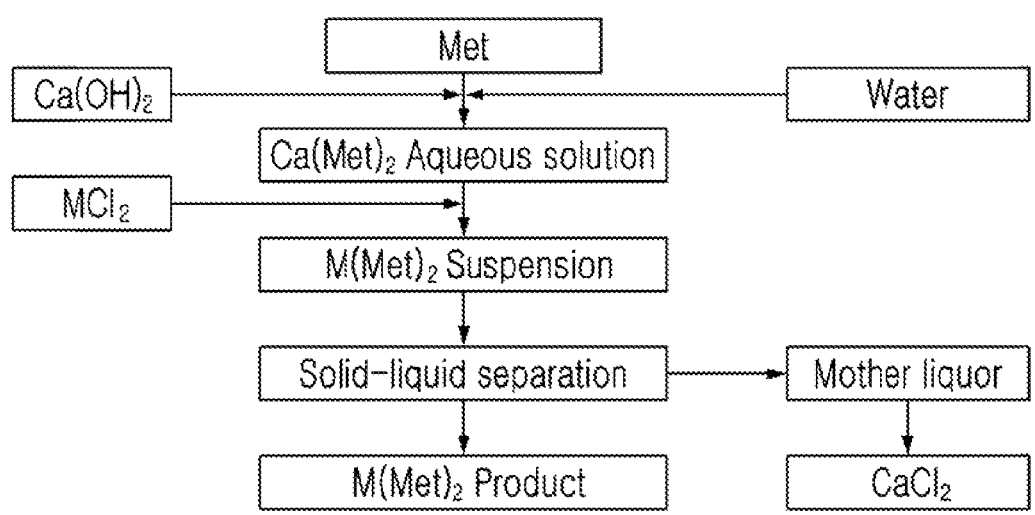

METHIONINE-METAL CHELATE AND MANUFACTURING METHOD THEREOF

CROSS-REFERENCE TO RELATED APPLICATIONS

This application is a U.S. National Stage application of PCT/KR2018/007691 filed 6 Jul. 2018, which claims priority to Korean Patent Application No. 10-2017-0089641 filed 14 Jul. 2017, the entire disclosures of which are herein incorporated by reference.

TECHNICAL FIELD

The present disclosure relates to a methionine-metal chelate and a preparation method thereof.

BACKGROUND ART

Although making up a very small proportion in animal tissues, mineral components such as zinc (Zn), manganese (Mn), copper (Cu), iron (Fe), etc., perform various physiological functions such as forming a skeleton, regulating osmotic pressure in the body, maintaining acid-base equilibrium of body fluids, being involved in the activity as an active agent of the enzymatic system or as a component of enzymes themselves, etc. For example, zinc is an essential material for the growth of livestock and contributes to boosting immunity.

Since such mineral components including zinc cannot be synthesized in the body, proper supply from the outside is necessary, and in the case of livestock, they are provided by combining these ingredients in feeds. However, when minerals are ingested in the inorganic form, such as metal oxides or metal salts, dissociated metal elements can form complexes with other elements competitively, and thus, there is a disadvantage that absorption is inhibited. Therefore, inorganic trace minerals are being supplied in excess of actual livestock demands, and excess minerals that are not absorbed by living organisms are excreted in powder and are reduced to soil, causing deep soil contamination. Therefore, in recent years, the supply of inorganic trace minerals has been limited, such as establishing a legal limit of mineral contents in feed to prevent heavy metal pollution in the environment.

As such, the use of organic trace minerals has been suggested as an alternative, because the absorption rate is high even with using a low amount, which can satisfy the metabolic capacity and reduce the excretion amount. Representative product groups of such organic trace minerals are amino acid-metal complexes and amino acid-metal chelates. Studies are in progress on amino acid-metal chelates, which have relatively high absorption rates in the body.

For example, there are a preparation method of methionine-zinc chelate by mixing methionine with zinc chloride and then adding NaOH (U.S. Pat. No. 7,087,775), a preparation method of methionine-zinc chelate by simultaneously reacting methionine with calcium hydroxide and sulfur zinc sulfate (U.S. Pat. No. 6,710,079), a preparation method of methionine-mineral chelate by mixing a methionine solution and a mineral solution to which a basic substance is added (Korean Patent No. 10-0583274), a preparation method of yeast-mineral chelate by using a yeast liquid and mineral sulfate (Korean Patent No, 10-0860778), a preparation method of methionine-iron chelate by reacting an inorganic iron solution and a methionine solution at a predetermined temperature and pH (Korean Patent No. 10-0509141), etc. However, ions present in the metal salts used in these methods, such as sulfate ions, etc., have a disadvantage of forming a by-product such as insoluble salts or lowering the yield by interfering with the chelate bond between methionine and the metal.

DISCLOSURE

Technical Problem

As a result of making intensive efforts to find ways to produce methionine-metal chelates with high efficiency, the present applicant confirmed that the preparation method of the present disclosure does not generate insoluble salts and has an effect of greatly improving the recovery rate of the desired methionine-metal chelate, thereby completing the present disclosure.

Technical Solution

An object of the present disclosure is to provide a method for preparing a methionine-metal chelate, comprising mixing methionine and $Ca(OH)_2$; and adding metal chloride salts to the mixture to produce a methionine-metal chelate.

Another object of the present disclosure is to provide a methionine-metal chelate prepared by the preparation method above.

Still another object of the present disclosure is to provide a feed or a teed additive comprising the methionine-metal dictate.

Still another object of the present disclosure is to provide a method for preparing calcium chloride ($CaCl_2$), comprising mixing methionine and $Ca(OH)_2$, adding metal chloride salts to the mixture to produce a methionine-metal chelate; separating the produced methionine-metal chelate; and concentrating a filtrate from which the methionine-metal chelate is separated.

Advantageous Effect

The preparation method of methionine-metal chelates in the present disclosure can be widely used in the feed or feed additive industry of livestock, because the formation of insoluble salts as by-products is prevented, and the title compound can be obtained with high efficiency without additional processes for removing the insoluble salts above.

BRIEF DESCRIPTION OF DRAWINGS

The FIGURE is a diagram schematically illustrating a process for preparing a methionine-metal chelate using metal chloride salts as a metal raw material.

BEST MODE

In one aspect of achieving the object above, the present disclosure provides a method for preparing a methionine-metal chelate, comprising mixing methionine and $Ca(OH)_2$; and adding metal chloride salts to the mixture to produce a methionine-metal chelate.

The present disclosure rests on discovering that in preparing methionine-metal chelates, the recovery rate of methionine-metal chelates can be significantly improved compared to the existing method of using sodium hydroxide or hydrochloride, when methionine is first reacted with calcium hydroxide or calcium oxide to form a methionine-calcium chelate and then reacted with chloride of the desired metal to prepare a methionine-metal chelate. Further, as CaCl$_2$ is formed as a by-product from the preparation method of the present disclosure, it can be used as a deicer or refrigerant, etc. by additionally performing a step of concentrating a filtrate from which methionine-metal chelates are separated, and thus an environmentally friendly process can be provided that can minimize the generation of metal waste.

As used herein, the term "methionine-metal chelate" may be a compound having a heterocyclic ring structure in which metal ions and methionine are bonded by coordinate covalent bonds and ionic bonds. For example, when the metal is a divalent metal such as zinc, methionine-zinc chelate may be formed in a structure as shown in Chemical Formula 1 by combining methionine and zinc at a molar ratio of 2:1.

[Chemical Formula 1]

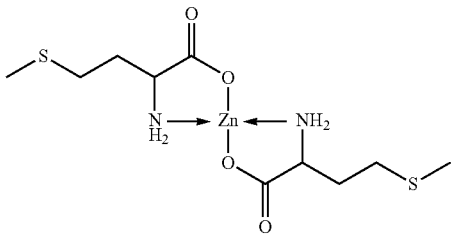

As shown in Chemical Formula 1 above, methionine-metal chelate compounds are not charged, which contributes to increased bioavailability. In addition, even when used less compared to inorganic trace minerals, their in vivo absorption rates are high, and it can help to prevent environmental pollution by satisfying the metabolic capacity and reducing the amount of minerals excreted in livestock excrements.

As used herein, the term "methionine" is one type of essential amino acids in living organisms, and it is an important amino acid involved in the in vivo methyl transfer reaction and serves to provide sulfur to living organisms. The methionine may be L-methionine or DL-methionine, and may be used in an aqueous methionine solution in the preparation method of the present disclosure. For example, the methionine aqueous solution may be a methionine aqueous solution prepared by using water, specifically, distilled water as a solvent. In this case, the concentration of methionine may be, for example, 50 g/L to 300 g/L, specifically, 120 g/L to 240 g/L, but is not limited thereto.

In the preparation method of the present disclosure, the step of mixing methionine and Ca(OH)$_2$ may be performed by heating as needed to completely dissolve methionine. The heating temperature may be 100° C. or less, specifically, 50° C. or less, but is not limited thereto.

As used herein, the term "metal chloride salts" is a compound composed of metal ions and nitrate ions represented by the formula MCl$_x$ (x=an integer of 1 to 6), and the number of chloride ions bound to the metal can be determined by the type of metals and/or oxidation number. For example, the metal in the metal chloride salts may be one or more metal selected from the group consisting of copper (Cu), zinc (Zn), manganese (Mn), magnesium (Mg), chromium (Cr), cobalt (Co), and iron (Fe). For example, the metal chloride salts may be CuCl$_2$, ZnCl$_2$, MnCl$_2$, MgCl$_2$, CrCl$_2$, CoCl$_3$, FeCl$_2$, or FeCl$_3$, but is not limited thereto. In addition, the metal chloride salts may be used in the form of anhydride or hydrate, but is not limited thereto. For example, in the case of zinc nitrate, ZnCl$_2$, which is an anhydride, or ZnCl$_2$·6H$_2$O, which is a hexahydrate can be used without limitation, and it does not affect the yield and/or the quality of the finally prepared methionine-zinc chelates.

For example, the metal chloride salts may be added at an equivalence ratio of 0.3 or more relative to methionine. Specifically, it can be added at an equivalence ratio of 0.3 or more and 3.0 or less, more specifically, 0.4 or more and 0.7 or less, but is not limited thereto. For example, when a metal chloride salts containing a divalent metal is used, assuming that all atoms and molecules participate in the reaction, two methionine molecules may bind to one metal atom as shown in Chemical Formula 1. Therefore, when metal chloride salts is added at an equivalence ratio of 0.5 relative to methionine, both methionine and the metal may appear to participate in the chelate formation. However, the equivalence ratio of metal chloride salts relative to methionine, which can exhibit an optimal yield depending on variables such as other ions substantially existing in the reaction solution, pH of the solution, temperature, etc. may be in the range above considering some errors based on the theoretical value of 0.5.

In addition, the preparation method of the present disclosure may further include purifying the generated methionine-metal chelate after producing a methionine-metal chelate. The purifying step may be carried out by a person skilled in the art to choose from known methods, for example, filtration, centrifugation, anion exchange chromatography, crystallization, HPLC, etc. may be used. For example, since calcium chloride, which is a by-product of the preparation method in the present disclosure, has high solubility in water, methionine-metal chelates whose solubility is relatively low may be separated using a solid-liquid separator, for example, a filtration, centrifugal, etc. solid-liquid separator, but is not limited thereto.

Furthermore, the preparation method of the present disclosure may further include drying a methionine-metal chelate. The drying step may be carried out using any method known in the art without limitation. For example, methods such as natural drying, heat drying, air drying, hot air drying, spray drying, drum drying, or rotary vacuum drying, etc. may be used, but are not limited thereto.

Specifically, upon spray drying, white powder can be obtained by drying under the conditions of inlet temperature of 180° C., outlet temperature of 90° C., and upon drying using a drum drier, white powder can be obtained by drying under the conditions of an internal temperature of 150° C. and a pressure of about 3 kgf/cm$^2$, and upon drying in a rotary vacuum drier, white powder can be obtained by vacuum drying under the conditions of an internal temperature of 55° C. to 70° C. and a vacuum of 650 mm/Hg.

In another aspect, the present disclosure provides a methionine-metal chelate prepared by the preparation method above.

In another aspect, the present disclosure provides a feed or a feed additive including the methionine-metal chelate.

As used herein, the term "feed" refers to food that is ingested by an animal, and specifically, may refer to a material that supplies organic or inorganic nutrients necessary to maintain the life of the animal or to produce meat, milk, etc. The feed may include feed additives and may be prepared in various forms known in the art.

The type of the feed is not particularly limited, and a feed that is conventionally used in the corresponding technical field may be used. Non-limiting examples of the feed include vegetable feeds such as cereals, root plants, food processing by-products, algae, fibers, oils, starches, gourds, grain by-products, etc.; and animal feeds such as proteins, inorganics, fats and oils, minerals, single-cell proteins, zooplankton, or food, etc. These may be used alone or in combination of two or more thereof.

As used herein, the term "feed additive" refers to a substance added to a feed composition. The feed additive may be to improve productivity or promote health of a target animal, but is not limited thereto. The feed additive may correspond to a supplementary feed under the Control of Livestock and Fish Feed Act.

The feed additive of the present disclosure may be used by further mixing one or more ingredients of organic acids such as citric acid, fumaric acid, adipic acid, lactic acid, etc. and natural antioxidants such as polyphenols, catechins, tocopherols, vitamin C, green tea extract, chitosan, tannic acid, etc., and depending on needs, other conventional additives such as buffers, bacteriostatic agents, etc. may be added. In addition, it may be formulated into a liquid, capsule, granule, or tablet as needed.

The teed or feed additive may further include substances exhibiting various effects such as supplementation of nutrients and prevention of weight loss, enhancement of digestive availability of fibers in the feed, improvement of oil quality, prevention of reproductive disorders and improvement in conception rates, prevention of high-temperature stress in summer, etc. For example, it may be used with nutritional supplements, growth promoters, digestive absorption accelerators, and disease prevention agents, in addition to the main components such as various supplements such as amino acids, inorganic salts, vitamins, antioxidants, antifungal, microbial preparations, etc., vegetable protein feeds such as milled or crushed wheat, barley, corn, etc., animal protein feeds such as powdered blood, powdered meat, powdered fish, etc., animal fats and vegetable fats.

The feed and feed additive of the present disclosure may be fed to a number of animals, including mammals and poultry. These can be used in commercially important mammals such as pigs, cattle, goats, etc., and livestock such as dogs, cats, etc., but are not limited thereto.

In another aspect, the present disclosure provides a method for preparing calcium chloride ($CaCl_2$), comprising mixing methionine and $Ca(OH)_2$; adding metal chloride salts to the mixture to produce a methionine-metal chelate separating the produced methionine-metal chelate; and concentrating a filtrate from which the methionine-metal chelate is separated.

The preparation method of calcium chloride in the present disclosure may further include a step of granulating after the concentrating step, but is not limited thereto. The granulating step may be carried out using any method known in the art without limitation.

As previously described, in the step of mixing methionine and CaO or $Ca(OH)_2$ and the step of producing a methionine-metal chelate by adding metal chloride salts to the mixture, a methionine-metal chelate which is the title compound and $CaCl_2$ which is a by-product are produced. Since the $CaCl_2$ is a water-soluble substance and has a significantly higher solubility than methionine-metal chelates, methionine-metal chelates may be selectively crystallized by adjusting the temperature of the solution, etc. As a filtrate from which methionine-metal chelates are separated has a large amount of $CaCl_2$, which is a by-product, dissolved therein, $CaCl_2$ can be obtained from a mother liquor through an additional process of concentrating and/or selectively granulating. In addition to helping to reduce process waste, $CaCl_2$ prepared as above can be used as a deicer and refrigerant, thereby creating additional economic values.

DETAILED DESCRIPTION

Hereinafter, the present disclosure will be described in more detail in the following examples. However, these examples are only to help the understanding of the present disclosure, and the present disclosure is not limited thereto.

Comparative Example 1: Preparation of Methionine-Zinc Chelate According to Method of Adding NaOH After Dissolving Metal Salt and Methionine A methionine-zinc chelate was prepared using the method described in U.S. Pat. No. 7,087,775. Specifically, 2. L of $ZnCl_2$ aqueous solution was prepared, and L-methionine was dissolved in $ZnCl_2$:L-methionine=1:2 molar ratio so that the concentration of L-methionine was 120 g/L. NaOH was added to the corresponding aqueous solution in the same equivalence ratio as L-methionine to prepare a suspension containing L-methionine-zinc chelate particles. The corresponding suspension was separated by vacuum filter to obtain L-methionine-zinc chelate. After drying, the content was 79.1% methionine and 17.8% zinc, and in this case, the recovery rate based on methionine was 78.3%.

Comparative Example 2: Preparation of Methionine-Zinc Chelate According to Method of Synthesis by Simultaneously Mixing $Ca(OH)_2$/Metal Sulfate/Methionine A methionine-zinc chelate was prepared by using the method described in U.S. Pat. No. 6,710,079. Specifically, 120 g of L-methionine was mixed with $Ca(OH)_2$ and $ZnSO_4$ heptahydrate at an equivalence ratio of 0.5 relative to L-methionine to prepare a powder mixture. The corresponding mixture was placed in a closed container and reacted at 80° C. for 12 hours. After cooling to room temperature, a mixture of L-methionine chelate and $CaSO_4$ was obtained. After drying, the content was 59.2% methionine. 13.0% zinc, 7.8% calcium, and 18.0% $SO_4$, and the purity calculated by adding the contents of methionine and zinc was 73.7%.

Comparative Example 3: Preparation of Methionine-Manganese Chelate According to Method of Adding NaOH After Dissolving Metal Salt and Methionine A methionine-manganese chelate was prepared using the method described in U.S. Pat. No. 7,087,775. Specifically, 2 L of $MnCl_2$ aqueous solution was prepared, and L-methionine was dissolved in $MnCl_2$:L-methionine=1:2 molar ratio so that the concentration of L-methionine was 120 g/L. NaOH was added to the corresponding aqueous solution in the same equivalence ratio as L-methionine to prepare a suspension including L-methionine-manganese chelate particles. The corresponding suspension was separated by a vacuum filter to obtain L-methionine-manganese chelate. After drying, the content was 67.2% methionine and 8.8% manganese, and in this case, the recovery rate based on methionine was 7.1%.

Comparative Example 4: Preparation of Methionine-Iron Chelate According to Method of Adding NaOH After Dissolving Metal Salt and Methionine A methionine-iron chelate was prepared using the method described in U.S. Pat. No. 7,087,775. Specifically, 2 L of FeCl$_2$ aqueous solution was prepared, and L-methionine was dissolved 2/L. NaOH was added to the corresponding aqueous solution in the same equivalence ratio as L-methionine to prepare a suspension including L-methionine-iron chelate particles. The corresponding suspension was separated by vacuum filter to obtain L-methionine-iron chelate. After drying, the content was 64.9% methionine and 9.2% iron, and in this case, the recovery rate based on methionine was 14.8%.

Comparative Example 5: Preparation of Methionine-Copper Chelate According to Method of Adding NaOH After Dissolving Metal Salt and Methionine A methionine-copper chelate was prepared using the method described in U.S. Pat. No. 7,087,775. Specifically, 2 L of CuCl$_2$ aqueous solution was prepared, and L-methionine was dissolved in CuCl$_2$:L-methionine=1:2 molar ratio so that the concentration of L-methionine was 120 g/L. NaOH was added to the corresponding aqueous solution in the same equivalence ratio as L-methionine to prepare a suspension including L-methionine-copper chelate particles. The corresponding suspension was separated by vacuum filter to obtain L-methionine-copper chelate. After drying, the content was 82.4% methionine and 16.8% copper, and in this case, the recovery rate based on methionine was 28.9%.

Example 1: Preparation of Methionine-Zinc Chelate According to Method of Adding Metal Chloride Salts After First Dissolving Ca(OH)$_2$ and Methionine (Met:Zn=1:0.4)

An L-methionine-calcium chelate aqueous solution was prepared by adding Ca(OH)$_2$ at an equivalence ratio of 0.5 relative to the L-methionine in 2 L of an aqueous suspension of L-methionine concentration 58 g/L. Thereafter, ZnCl$_2$, which is an anhydride, was added to the corresponding aqueous solution at an equivalence ratio of 0.4 relative to L-methionine, thereby obtaining L-methionine-zinc chelate. After drying, the content was 80.8% methionine and 18.4% zinc, and in this case, the recovery rate based on methionine was 94.5%.

Example 2: Preparation of Methionine-Zinc Chelate According to Method of Adding Metal Chloride Salts After First Dissolving Ca(OH)$_2$ and Methionine (Met:Zn=1:0.5)

An L-methionine-calcium chelate aqueous solution was prepared by adding Ca(OH)$_2$ at an equivalence ratio of 0.5 relative to the L-methionine in 2 L of an aqueous suspension of L-methionine concentration 58 g/L. Thereafter, ZnCl$_2$, which is an anhydride, was added to the corresponding aqueous solution at an equivalence ratio of 0.5 relative to L-methionine, thereby obtaining an L-methionine-zinc chelate. After drying, the content was 81.2% methionine and 18.0% zinc, and in this case, the recovery rate based on methionine was 93.7%.

Example 3: Preparation of Methionine-Zinc Chelate According to Method of Adding Metal Chloride Salts After First Dissolving Ca(OH)$_2$ and Methionine (Met:Zn=1:0.7)

L-methionine-calcium chelate aqueous solution was prepared by adding Ca(OH)$_2$ at an equivalence ratio of 0.5 relative to the L-methionine in 2 L of an aqueous suspension of L-methionine concentration 58 g/L. Thereafter, ZnCl$_2$, which is an anhydride, was added to the corresponding aqueous solution at an equivalence ratio of 0.7 relative to L-methionine, thereby obtaining an L-methionine-zinc chelate, After drying, the content was 81.1% methionine and 18.4% zinc, and in this case, the recovery rate based on methionine was 95.2%.

Example 4: Preparation of DL-Methionine-Zinc Chelate According to Method of Adding Metal Chloride Salts After First Dissolving Ca(OH)$_2$ and DL-Methionine A DL-methionine-calcium chelate aqueous solution was prepared by adding Ca(OH)$_2$ at an equivalence ratio of 0.5 relative to the DL-methionine in 2 L of an aqueous suspension of DL-methionine concentration 154 g/L. Thereafter. ZnCl$_2$, which is an anhydride, was added to the corresponding aqueous solution at an equivalence ratio of 0.5 relative to DL-methionine, thereby obtaining a DL-methionine-zinc chelate. After drying, the content was 81.1% methionine and 17.9% zinc, and in this case, the recovery rate based on methionine was 94.5%.

Example 5: Preparation of Methionine-Manganese Chelate According to Method of Adding Metal Chloride Salts After First Dissolving Ca(OH)$_2$ and Methionine An L-methionine-calcium chelate aqueous solution was prepared by adding Ca(OH)$_2$ at an equivalence ratio of 0.5 relative to the L-methionine in 2 L of an aqueous suspension of L-methionine concentration 120 g/L. Thereafter, MnCl$_2$.4H$_2$O was added to the corresponding aqueous solution at an equivalence ratio of 0.5 relative to L-methionine, thereby obtaining an L-methionine-manganese chelate. After drying, the content was 83.5% methionine and 15.6% manganese, and in this case, the recovery rate based on methionine was 67.3%.

Example 6: Preparation of Methionine-Iron Chelate According to Method of Adding Metal Chloride Salts After First Dissolving Ca(OH)$_2$ and Methionine An L-methionine-calcium chelate aqueous solution was prepared by adding Ca(OH)$_7$, at an equivalence ratio of 0.5 relative to the L-methionine in 2 L of an aqueous suspension of L-methionine concentration 120 g/L. Thereafter, FeCl$_2$.4H$_2$O was added to the corresponding aqueous solution at an equivalence ratio of 0.5 relative to L-methionine, thereby obtaining an L-methionine-iron chelate. After drying, the content was 70.9% methionine and 11.1% iron, and in this case, the recovery rate based on methionine was 43.7%.

Example 7: Preparation of Methionine-Copper Chelate According to Method of Adding Metal Chloride Salts After First Dissolving Ca(OH)$_2$ and Methionine An L-methionine-calcium chelate aqueous solution was prepared by adding Ca(OH)$_2$ at an equivalence ratio of 0.5 relative to the L-methionine in 2 L of an aqueous suspension of L-methionine concentration 120 g/L. Thereafter, CuCl$_2$.2H$_2$O was added to the corresponding aqueous solution at an equivalence ratio of 0.5 relative to L-methionine, thereby obtaining an L-methionine-copper chelate. After drying, the content was 81.9% methionine and 17.4% copper, and in this case, the recovery rate based on methionine was 49.2%.

Example 8: Preparation of $CaCl_2$ Using Methionine-Metal Chelate Reaction by-Product After preparing an L-methionine-zinc chelate according to Example 2 above, the title compound, L-methionine-zinc chelate, was separated and the remaining mother liquor was further concentrated 15 times with a rotary evaporator to prepare a concentrate including $CaCl_2$, a by-product of the reaction, as a main component. The moisture in the concentrate obtained using a fluid bed granulator was removed, and then $CaCl_2$ granular particles were prepared. After drying the corresponding granular particles, the content was 33.1% calcium and 57.9% chloride.

From a series of the comparative examples and examples above, compared to the method of adding NaOH in the mixture of metal salts and methionine, which is a conventional preparation method of a methionine-metal chelate, or the method of using metal sulfate, it was confirmed that the recovery rate of a methionine-metal chelate could be significantly increased by using a preparation method of reacting with metal chloride salts after forming the methionine-calcium chelate of the present disclosure. Specifically, in Comparative Example 1 using NaOH, the recovery rate of the methionine-zinc chelate, which was derived based on methionine, was 78.3%. In Comparative Example 2 using sulfate, the recovery rate was only 73.7%. However, in Example 2 in which methionine and a zinc compound were reacted at the same molar ratio using the preparation method of the present disclosure, the significantly high recovery rate of 93.7% was shown.

Meanwhile, as a result of changing the type of metal to prepare a methionine-metal chelate and confirming the recovery rate thereof, compared to preparing a methionine-metal chelate using the conventional method of using NaOH as in Comparative Examples 3 to 5, a methionine-manganese chelate, a methionine-iron chelate, and a methionine-copper chelate were prepared at increased recovery rates of 60.2%, 28.9%, and 20.3%, respectively, when prepared according to Examples 5 to 7 of the present disclosure.

Further, in the preparation process of a methionine-metal chelate according to the present disclosure, a methionine-metal chelate which is the title compound was recovered from the reaction solution, and the remaining mother liquor contained $CaCl_2$ as a main component, and it was confirmed that as in Example 8, $CaCl_2$ was obtained in the form of granular particles by concentrating and granulating the mother liquor.

As such, the process of the present disclosure can prepare a methionine-metal dictate at a high yield, which can be used as teed and feed additive, and $CaCl_2$ which is produced as a by-product of the process can be utilized as a deicer or refrigerant, etc. by granulation through concentration and an additional granulation process.

From the above description, those skilled in the art will appreciate that the present disclosure can be implemented in other specific forms without changing the technical spirit or essential features. In this regard, the examples described above are illustrative in all respects and should be understood as not limiting. The scope of the present disclosure should be construed as including the meaning and scope of the following claims rather than the detailed description, and all changes or modifications derived from the equivalent concepts.

The invention claimed is:

1. A method for preparing a neutral methionine-metal chelate, comprising:
   mixing methionine and $Ca(OH)_2$; and
   adding one or more metal chloride salts to the mixture to produce the neutral methionine-metal chelate,
   wherein the methionine-metal chelate has structure of Chemical formula 1;

[Chemical formula 1]

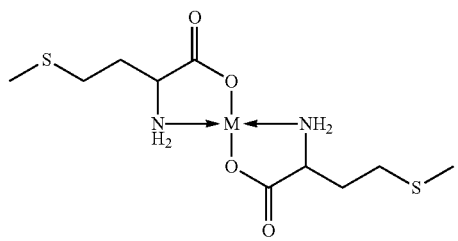

wherein M is a metal from the one or more metal chloride salts.

2. The method of claim 1, wherein the methionine is L-methionine or DL-methionine.

3. The method of claim 1, wherein metals in the one or more metal chloride salts are one or more metals selected from the group consisting of copper (Cu), zinc (Zn), manganese (Mn), and iron (Fe).

4. The method of claim 1, wherein the one or more metal chloride salts are added at an equivalence ratio of 0.3 to 3.0.

5. The method of claim 1, further comprising purifying the produced methionine-metal chelate.

6. The method of claim 1, wherein the methionine is used in an aqueous methionine solution, and further comprising drying the methionine-metal chelate.

7. A method for preparing calcium chloride ($CaCl_2$), comprising:
   mixing an aqueous methionine solution and $Ca(OH)_2$;
   adding one or more metal chloride salts to the mixture to produce a neutral methionine-metal chelate;
   separating an aqueous solution comprising the neutral methionine-metal chelate and calcium chloride ($CaCl_2$) via filtration to produce a filtrate from which the neutral methionine-metal chelate has been removed; and
   concentrating the filtrate to obtain calcium chloride ($CaCl_2$);
   and wherein the neutral methionine-metal chelate has structure of Chemical formula 1;

[Chemical formula 1]

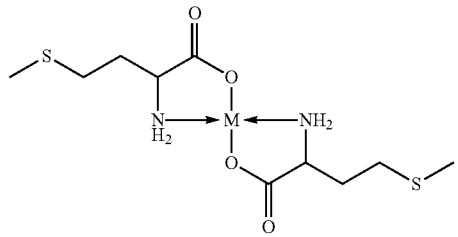

wherein M is a metal from the one or more metal chloride salts.

8. The method of claim 7, wherein metals in the one or more metal chloride salts are one or more metals selected from the group consisting of copper (Cu), zinc (Zn), manganese (Mn), and iron (Fe).

9. The method of claim 7, further comprising granulating the calcium chloride after the concentrating.

* * * * *

UNITED STATES PATENT AND TRADEMARK OFFICE
CERTIFICATE OF CORRECTION

PATENT NO.          : 11,072,621 B2              Page 1 of 1
APPLICATION NO.     : 16/630902
DATED               : July 27, 2021
INVENTOR(S)         : Jun-Woo Kim et al.

It is certified that error appears in the above-identified patent and that said Letters Patent is hereby corrected as shown below:

On the Title Page

(73) Assignee, Lines 1-2, "GJ CHEILJEDANG CORPORATION" should be --CJ CHEILJEDANG CORPORATION--

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*